US006877985B2

(12) United States Patent
Lynch

(10) Patent No.: US 6,877,985 B2
(45) Date of Patent: Apr. 12, 2005

(54) USE OF OZONE TO WHITEN TEETH

(75) Inventor: Edward Lynch, Northern Ireland (GB)

(73) Assignee: Curozone Ireland Limited (IL)

( * ) Notice: Subject to any disclaimer, the term of this patent is extended or adjusted under 35 U.S.C. 154(b) by 228 days.

(21) Appl. No.: 10/196,854

(22) Filed: Jul. 17, 2002

(65) Prior Publication Data
US 2003/0082500 A1 May 1, 2003

Related U.S. Application Data
(60) Provisional application No. 60/309,570, filed on Aug. 2, 2001.

(51) Int. Cl.[7] ............................................. A61C 15/00
(52) U.S. Cl. ...................................................... 433/216
(58) Field of Search ................................ 433/215, 216, 433/136, 91

(56) References Cited

U.S. PATENT DOCUMENTS

| | | | |
|---|---|---|---|
| 3,882,865 A | 5/1975 | Hatzitheodorou | |
| 4,021,921 A | 5/1977 | Detaille | |
| 4,422,450 A * | 12/1983 | Rusteberg | 601/162 |
| 4,438,100 A | 3/1984 | Balslev et al. | |
| 4,743,199 A | 5/1988 | Weber et al. | |
| 4,991,570 A | 2/1991 | Bullard | |
| 5,055,043 A | 10/1991 | Weiss et al. | |
| 5,197,876 A | 3/1993 | Coston | |
| 5,356,292 A | 10/1994 | Ho | |
| 5,505,914 A * | 4/1996 | Tona-Serra | 422/186.12 |
| 5,547,376 A | 8/1996 | Harrel | |
| 5,942,125 A | 8/1999 | Engelhard et al. | |
| 6,305,936 B1 * | 10/2001 | Jensen et al. | 433/136 |
| 6,479,037 B1 * | 11/2002 | Montgomery | 424/53 |
| 6,545,566 B2 | 4/2003 | Lynch et al. | |
| 2002/0172707 A1 * | 11/2002 | Joyce | 424/439 |

FOREIGN PATENT DOCUMENTS

| | | |
|---|---|---|
| DE | 3825824 A1 | 2/1990 |
| WO | WO 99/64020 | 12/1999 |

* cited by examiner

Primary Examiner—Todd E. Manahan
(74) Attorney, Agent, or Firm—Walter A. Hackler

(57) ABSTRACT

Method and apparatus for the whiting of teeth includes a source of oxidizing gas and a handpiece for delivering the gas to a tooth. A cup attached to the handpiece is provided for receiving the gas and exposing a selected area of the tooth to the gas. The cup includes a resilient edge for sealably the edge for engaging the tooth around the selected area to prevent escape of a gas therepast.

6 Claims, 3 Drawing Sheets

US 6,877,985 B2

USE OF OZONE TO WHITEN TEETH

This application claims priority from provisional application Ser. No. 60/309,570 filed Aug. 2, 2001.

The present invention generally relates to a method for whitening teeth, and more particularly, relates to a method for whitening teeth which utilizes ozone.

White teeth have long been considered cosmetically desirable. Typically, a tooth becomes discolored in specific regions, or spots, and in overall color. Tooth materials which are generally responsible for presenting a stained appearance are enamel, dentin, and the acquired pellicle.

In particular, tooth enamel is formed predominantly from inorganic material, mostly in the form of hydroxyapatite crystals, and further contains approximately 5% organic material, primarily in the form of collagen. Conversely, dentin is composed of about 20% protein, including collagen, with the balance comprising of inorganic material, predominantly hydroxyapatite crystals, similar to that found in enamel. The acquired pellicle, on the other hand, is a proteinaceous layer on the surface of tooth enamel which reforms rapidly even following an intensive tooth cleaning with highly abrasive prophylaxis pastes.

Tooth discoloration results from both extrinsic and intrinsic staining. Extrinsic staining of the tooth surface arises as a result of the accumulation of various chromogenic substances (in addition to chromogen precursors, which are initially colorless, but later chemically convert to chromogens) within the acquired pellicle. This type of staining can usually be removed by mechanical methods, which remove the acquired pellicle or portions thereof, along with the adherent chromogens.

Aging of extrinsic stains, however, has been known to make the extrinsic stains less susceptible to removal by mechanical means, perhaps due, to increased depth of extrinsic stain penetration into enamel over time. Such stains, therefore, require the use of chemicals, such as oxygenating agents, which can penetrate the tooth enamel to oxidize or solubilize the deep-seated chromogens.

In contrast, intrinsic staining occurs as a result of chromogenic substances derived from sources within the tooth. This type of staining is not amenable to mechanical methods of tooth cleansing, and the aforementioned chemical methods are usually required. Further variations in tooth composition including filling material can contribute to variation in coloration density resulting in darkened area.

Tooth-whitening compositions generally fall into two categories: (1) liquids, gels, or pastes including toothpastes, that may be mechanically agitated at the stained tooth surface in order to effect tooth stain removal through abrasive erosion of stained acquired pellicle; and (2) liquids, gels, or pastes that accomplish the tooth-whitening effect by a chemical process while being in contact with the stained tooth surface for a specific period, after which the formulation is removed. In some cases the mechanical process is supplemented by an auxiliary chemical process, which may be oxidative or enzymatic.

Conventional teeth whitening typically utilizes a rubber sheet or dam for isolating teeth. The dam is typically made from latex rubber and forced over each tooth and held in place with conventional clamps and ligatures. This is done to protect the soft tissue of the gums from peroxides typically used in the bleaching procedure.

However, since the rubber sheet or dam does not provide a perfect fit and can stretch, peroxide can leak therearound and cause discomfort to the patient. In order to expedite the procedure after a peroxide solution is coated onto the teeth, heat is applied or the coated teeth are exposed to laser radiation. Exposure to heat also may cause discomfort to the patient if the pulp temperature within the tooth becomes too high. As a result, a number of appointments are required.

The present invention overcomes the disadvantages of the prior art by utilization of ozone for whitening teeth which enables both total tooth whitening a "spot" whitening of a tooth.

SUMMARY OF THE INVENTION

A method for whitening teeth in accordance with the present invention comprises the steps of isolating the teeth to be whitened and exposing each for the isolated teeth to ozone. The method may be applied over a number of teeth or an individual tooth. Further, as hereinabove noted, portions of a tooth may also be whitened in accordance with the method of the present invention.

BRIEF DESCRIPTION OF THE DRAWINGS

The advantages and features of the present invention will be better understood by the following description when considered in conjunction of the accompanying drawings, in which.

DETAILED DESCRIPTION

Figure 1:
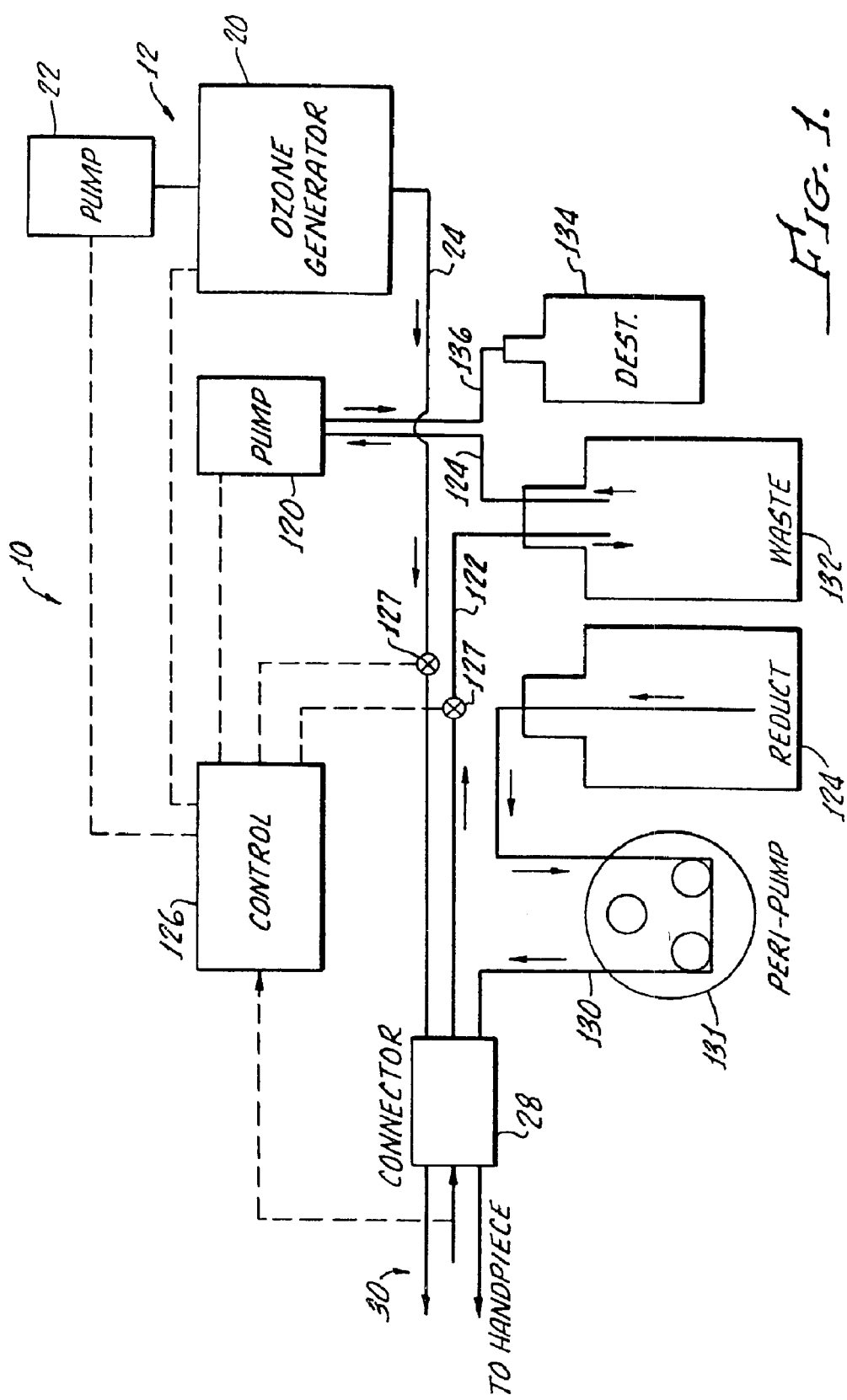
FIG. 1 illustrates a block diagram of apparatus for whitening teeth in accordance with the present invention, the apparatus generally includes a source of oxidizing gas, an aspiration pump, a source of reductant, a reductant pump and a controller for providing the oxidizing gas to a handpiece.
Figure 2:
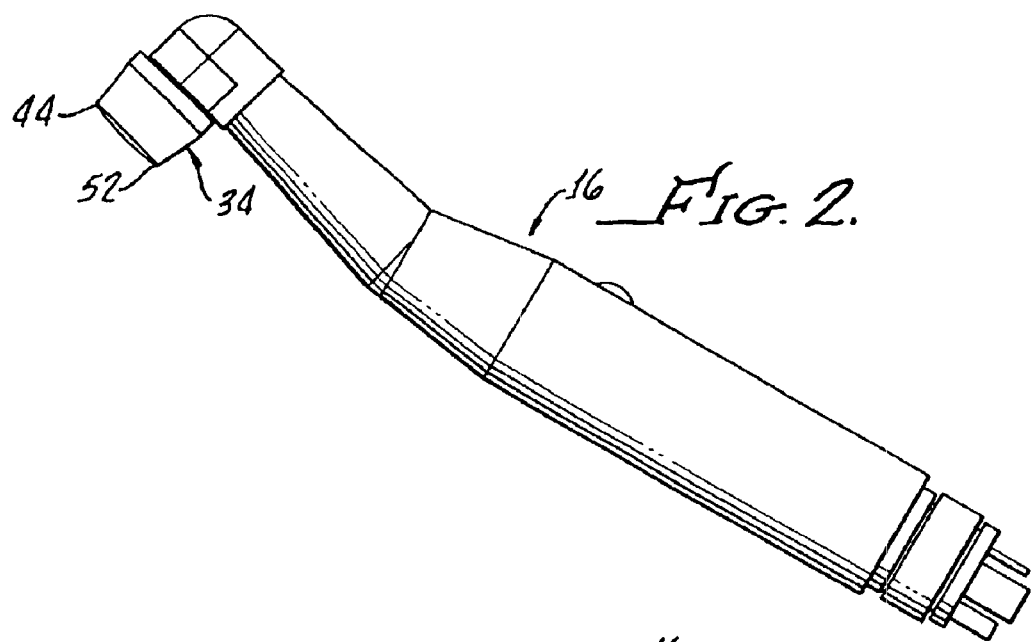
FIG. 2 illustrated a handpiece in accordance with the present invention for delivering a gas to a tooth and generally showing a cup attached to the handpiece for receiving the gas.
Figure 3:
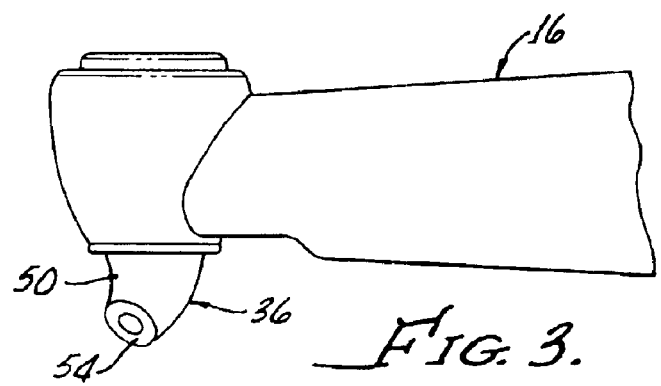
FIG. 3 illustrated the handpiece with an alternative cup embodiment, the alternative embodiment cup having an arcuate shape for facilitating application of oxidizing gas to a tooth.

With reference to FIGS. 1–4, there is shown apparatus 10 in accordance with the present invention for the whitening of teeth which includes a source 12 of oxidizing gas, preferably ozone, and a handpiece 16 (see FIG. 2) for delivering the gas to a tooth, not shown in FIGS. 1–3.

As illustrated in FIG. 1, the ozone source 12 includes an ozone generator 20 and an ozone pump 22 for supplying ozone through a line 24, a connector 28 and lines 30 to the handpiece 16. As used herein, the term "ozone" is intended to embrace any suitable oxidizing gas, pure ozone, ionized air and other ozone gaseous mixtures.

Ozone is delivered at a pressure, concentration and for a period of time sufficient to whiten tooth enamel.

As shown in FIGS. 2–3, cups 34, 36 attached to the handpiece 16 are provided for receiving the gas and exposing a selected area 38 on a tooth 40 for whitening, see FIG. 3. The cup 34 may be attached to the handpiece 16 in any conventional manner and include a resilient edge, or sidewall, 44 for sealable engaging the tooth 40 to prevent the escape of gas therepast.

Figure 4:
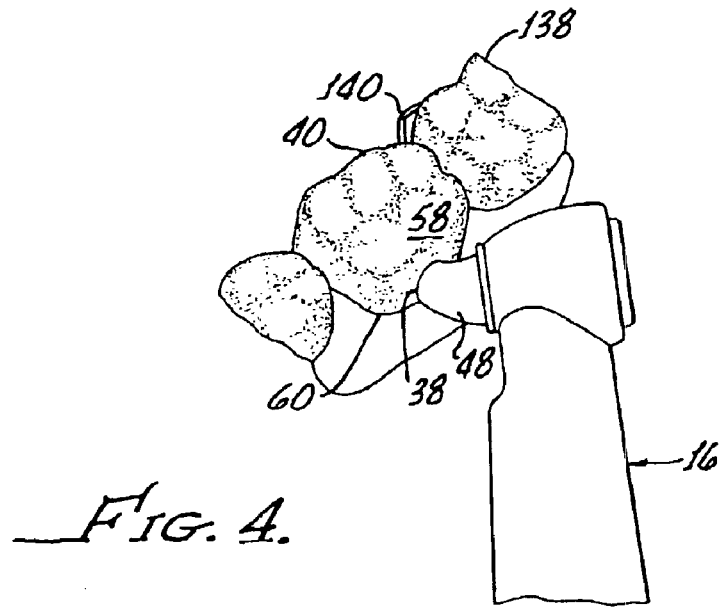
FIG. 4 is a diagram showing application of oxidizing gas to a tooth between a cusp and a gingival utilizing the handpiece and cup shown in FIG. 3.

Many different sized and shaped cups may be utilized to accommodate various tooth profiles or to apply ozone to specific spots or portions of a tooth. For example, as shown in FIG. 3 the cup 36 includes an arcuate trunk 50 to facilitate the placement of the cup 36 over the selected area 38 to be whitened as shown in FIG. 4. The cups 34, 36 may have relatively uniform perimeters 52, 54 for sealably engaging the tooth 40 between a cusp 58 and a gingiva 60 as shown in FIG. 4.

Figure 6:
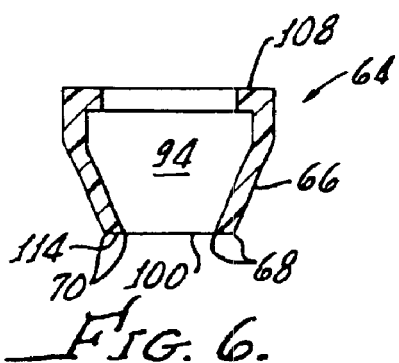
FIG. 6 is a cross-sectional view an alternative embodiment of a cup for exposing a selected area of a tooth oxidizing gas.

A further cup embodiment 64 is shown in cross-section in FIG. 6 includes a tapered sidewall 66 that may be used for application of oxidizing gas to a smaller selected area (not shown) on the tooth 40.

While a resilient edge or sidewall may be used to couple the cup to the selected area 38 on the tooth 40, it should be appreciated that a separate sealant 68 (See FIG. 6) may be utilized for providing a sealable engagement between the cup 64 and the tooth 40. In this instance, the sidewall 66 need not be resilient.

The use of a handpiece and cap to provide ozone eliminates or significantly reduces gum exposure. Thus, less, if any irritation to the patient, by way of gum exposure occurs. This enables the whitening of all of a patient's teeth during one appointment with a dentist.

Figure 7:
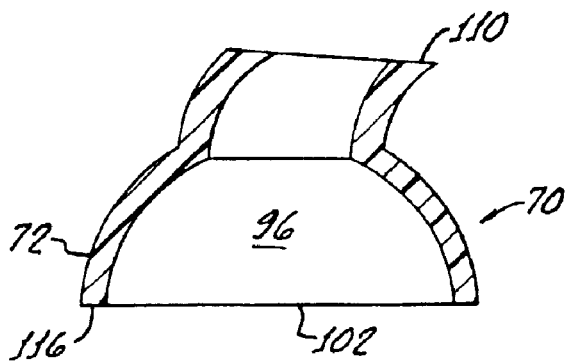
FIG. 7 is a cross-sectional diagram showing an alternative embodiment of a cup in accordance with the present invention for exposing adjacent teeth to oxidizing gas.
Figure 8:
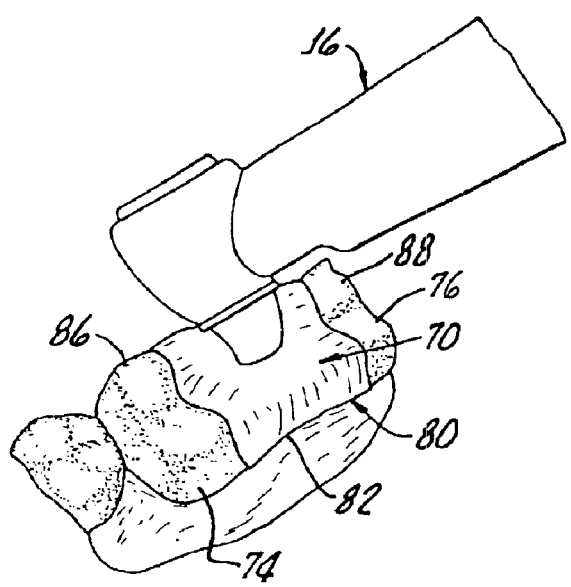
FIG. 8 illustrates the use of the cup shown in FIG. 7 as it may be applied to adjacent teeth.

Another embodiment of a cup 70 is shown in cross-section in FIG. 7 which includes walls 72 which are contoured for enabling the sealable engagement with adjacent teeth 74, 76 as shown in FIG. 8. As shown in FIG. 8, a cup edge 80 has a perimeter contour 82 for providing a sealable engagement with cups 86, 88 of adjacent teeth 74, 76.

Figure 5:
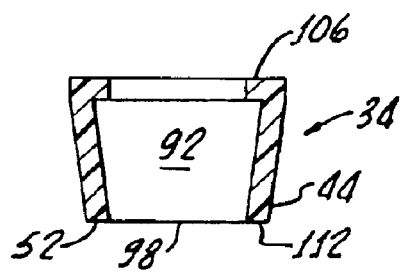
FIG. 5 is cross-sectional view of the cup shown in FIG. 2 that is suitable for use in the present invention.

All of the cups 34, 64, 70, cross-sectionally illustrated in FIGS. 5–7, include cup chambers 92, 94, 96 that subtend cup edges 98, 100, 102. As shown each of the cups 34, 64, 70 include walls 44, 66, 72 that define the chambers 92, 94, 96 and include first perimeters 106, 108, 110 for sealably coupling the walls 44, 66, 72 to the handpiece 16. Second perimeters 112, 114, 116 provide for coupling the walls 44,66 72 to the tooth 40 and exposing the selected areas 38 to gas circulated in the chambers 92, 94, 96.

As shown in FIG. 6, the embodiment 64 the first perimeter 108 may be larger than the second perimeter 115 or, as shown in FIG. 7, the first perimeter 110 may be smaller than the second perimeter 116. Accordingly this variation in cup 64, 70 design enables the application of oxidizing gas the any number of tooth contours and to the application of oxidizing gas to a plurality of teeth has hereinabove described.

With reference again to FIG. 1, the apparatus 12 includes an aspiration pump 120 and lines 30, 122, 124 connected to the handpiece 16 for enabling circulation of the ozone into and out of the cup chambers 92, 94, 96.

A controller 126, which may be of any conventional circuit design, is provided for regulating the ozone and aspiration pumps 22, 120 in order to circulate the gas into and out of the cup chambers 92, 94, 96 at a pressure insufficient to permit escape of the gas past a sealed engagement between the cups 34, 64, 70 and teeth 40, 86, 88. Control of the gas flows may also be effected through valves 127, regulated by the controller 126.

Additionally, the apparatus 10 may include a reductant source 128, which is in fluid communication with the cup chambers 92, 94, 96 through lines 30, 130 and a parastalic pump 131. The reductant, which may be a solution of thiocyanate or peppermint, is utilized to flush the cup chambers 92, 94, 96 of oxidizing gas. The oxidizing gas is flushed into the aspiration line 122 following ozone treatment of the tooth 40, 86, 88. The reductant is then aspirated through line 122 and into a waste accumulator 132.

Any residual ozone is then aspirated from the accumulator 132 through the line 124 and into a canister 134 through line 136 for final elimination of the ozone. Thus, the apparatus 12 provides for a totally closed system for the application and removal of ozone to and from teeth 40, 86, 88.

It should also be appreciate that when the cups 34, 36, 64 are utilized between teeth 40, 138 (not shown in FIG. 4) a separate dam 140 maybe utilized as necessary to enable the cups 34, 36, 64 (not shown in FIG. 4) to sealably enclose a selected area for treatment between the teeth 40, 138.

EXAMPLE 1

Ozone detection (ppm) around the cup using a ozone analyzer after either 10 or 20 s of ozone application in vivo Study or Test: Ozone detection (ppm) around the cup 34 using a ozone analyzer after either 10 or 20 s of ozone application in vivo Purpose:

To assess the maximum ozone detectable level (ppm) around the cup 34 after either 10 s or 20 s of ozone application in vivo.

Study or Test Protocol:

The tip of the sensor was always held within 2 mm of the edge of the cup, positioned half way between the mesial and occlusal sides of the cup. The maximum ozone detectable level (ppm) around the cup from the teeth is measured using an ozone analyzer after 10 s of ozone application. The ozone analyzer used was an API 450 model available from ENVIRO Technologies, UK, and was calibrated by the supplier within the previous week of delivery and this device was not used for any other purpose other than this study in the interim.

Overlying plaque was then removed using a hand held standard fine nylon fiber sterile toothbrush with water as a lubricant. Each tooth was dried using dry sterile cotton wool rolls and a dental 3 in 1-air syringe. Subsequently, the teeth are exposed to the ozone gas for a period of either 10 s or 20 s at room temperature (23° C.) and maximum detectable ozone level was also measured using this ozone analyzer.

Test Results:

The maximum ozone detectable level (ppm) expected around the cup for a period of either 10 s (FIG. 1) or 20 s (FIG. 2) ozone application.

TABLE 1

Maximum ozone detectable level (ppm) after a 10 s of ozone application

| Teeth types | Sites | Ozone detection (10 s) |
| --- | --- | --- |
| Upper left incisor | Mesial | 0.066 |
| Upper right 1. premolar | Buccal | 0.001 |
| Upper right canine | Distal | 0.002 |
| Upper right 1. molar | Buccal | 0.006 |
| Upper left 2. premolar | Buccal | 0.076 |
| Lower right 2. premolar | Mesial | 0.058 |
| Lower left 1. premolar | Buccal | 0.169 |

TABLE 1-continued

Maximum ozone detectable level (ppm) after a 10 s of ozone application

| Teeth types | Sites | Ozone detection (10 s) |
|---|---|---|
| Lower left lateral | Buccal | 0.106 |
| Upper right lateral | Distal | 0.001 |
| Lower left canine | Labial | 0.147 |

TABLE 2

Maximum ozone detectable level (ppm) after a 20 s of ozone application

| Teeth types | Sites | Ozone detection (20 s) |
|---|---|---|
| Lower left lateral | Labial | 0.137 |
| Lower left 1. premolar | Buccal | 0.177 |
| Lower right incisor | Labial | 0.069 |
| Upper right canine | Labial | 0.033 |
| Upper right lateral | Labial | 0.079 |
| Lower left 2. premolar | Buccal | 0.002 |
| Lower right 1. molar | Buccal | 0.083 |
| Upper left lateral | Labial | 0.004 |
| Lower left canine | Labial | 0.056 |
| Upper left 1. premolar | Mesial | 0.001 |

Conclusion:

The use of a cup is a safe way of delivering ozone when ozone was applied for a period of either 10 s or 20 s on a tooth for whitening teeth.

Although there has been hereinabove described method and apparatus for the treatment of dental caries as remineralized in accordance with the present invention for the purpose of illustrating the manner in which the invention may be used to advantage, it will be appreciated that the invention is not limited thereto. Accordingly, any and all modifications, variations or equivalent arrangements which may occur to those skilled in the art, should be considered to be within the scope of the invention as defined in the appended claims.

What is claimed is:

1. A method for whitening teeth comprising the steps of:
   isolating the teeth to be whitened;
   exposing each of the isolated teeth to an oxidizing gas for a period of time sufficient to whiten tooth enamel; and
   aspirating the oxidizing gas from the isolated tooth.

2. The method according to claim 1 wherein said oxidizing gas is ozone.

3. A method for whitening a tooth comprising the steps of:
   isolating a tooth to be whitened;
   exposing the isolated tooth to an oxidizing gas for a period of time sufficient to whiten the isolated tooth; and
   aspirating the oxidizing gas from the isolated tooth.

4. The method according to claim 3 wherein said oxidizing gas is ozone.

5. A method for whiting a tooth portion comprising the steps of:
   isolating a tooth portion to be whitened;
   exposing the isolated tooth portion to an oxidizing gas for a period of time sufficient to whiten the tooth portion; and
   aspirating the oxidizing gas from the isolated tooth portion.

6. The method according to claim 5 wherein said oxidizing gas is ozone.

* * * * *